(12) United States Patent
He

(10) Patent No.: US 10,241,053 B2
(45) Date of Patent: Mar. 26, 2019

(54) BACTERIAL DETECTION PLATFORM BASED ON SERS MAPPING

(71) Applicant: University of Massachusetts, Boston, MA (US)

(72) Inventor: Lili He, Belchertown, MA (US)

(73) Assignee: University of Massachusetts, Boston, MA (US)

( * ) Notice: Subject to any disclaimer, the term of this patent is extended or adjusted under 35 U.S.C. 154(b) by 61 days.

(21) Appl. No.: 15/173,098

(22) Filed: Jun. 3, 2016

(65) Prior Publication Data

US 2016/0356721 A1 Dec. 8, 2016

Related U.S. Application Data

(60) Provisional application No. 62/171,010, filed on Jun. 4, 2015, provisional application No. 62/170,381, filed on Jun. 3, 2015.

(51) Int. Cl.
| | | |
|---|---|---|
| *G01J 3/44* | (2006.01) | |
| *G01N 21/65* | (2006.01) | |
| *C12Q 1/04* | (2006.01) | |
| *C12Q 1/06* | (2006.01) | |

(52) U.S. Cl.
CPC ............. *G01N 21/658* (2013.01); *C12Q 1/04* (2013.01); *C12Q 1/06* (2013.01); *G01N 2333/32* (2013.01)

(58) Field of Classification Search
CPC .. G01N 21/658; G01N 2333/32; G01N 21/63; G01N 33/00; G01N 21/65; C12Q 1/04; C12Q 1/06; C12Q 1/6816; C12Q 1/68; G01J 3/32; G01J 3/44; B82Y 20/00; C12M 1/34; B01D 59/44
See application file for complete search history.

(56) References Cited

U.S. PATENT DOCUMENTS

| | | | |
|---|---|---|---|
| 4,847,198 A | 7/1989 | Nelson et al. | |
| 2006/0250613 A1* | 11/2006 | Demuth | G01J 3/32 356/301 |
| 2008/0149822 A1* | 6/2008 | Vertes | B82Y 20/00 250/282 |

(Continued)

OTHER PUBLICATIONS

Wang, Y. et al. Separation and detection of multiple pathogens in a food matrix by magnetic SERS nanoprobes, Anal. Bioanal. Chem (2011) 399:1271-1278.

(Continued)

*Primary Examiner* — Jamil Ahmed
(74) *Attorney, Agent, or Firm* — Schwegman Lundberg & Woessner, P.A.

(57) ABSTRACT

A bacterial detection platform integrating the sensitive SERS technique and the advanced mapping technique. Bacterial cells on the SERS substrate are detected using the mapping technique. The identification is based on the fingerprint of the bacterial SERS spectra. The quantification of the cells is based on the mapping technique. For different applications, silver or gold nanoparticles can be integrated onto a filter membrane for concentration and detection of bacterial cells in water or silver dendrites can be used as the SERS substrate. The SERS substrates are also modified with capturers and fixed in a vessel to concentrate cells from complex liquid matrices.

17 Claims, 14 Drawing Sheets

(56) References Cited

U.S. PATENT DOCUMENTS

2010/0151465 A1* 6/2010 Ju .................... C12Q 1/6816
435/6.12
2013/0107254 A1* 5/2013 Yu ..................... G01J 3/44
356/301

OTHER PUBLICATIONS

Yu, W.W. Inkjet Printed Paper Surface Enhanced Raman Spectroscopy Devices for Trace Chemical Analysis, Ph.D. Thesis, University of Maryland, 2013.

* cited by examiner

FIG. 5a-b

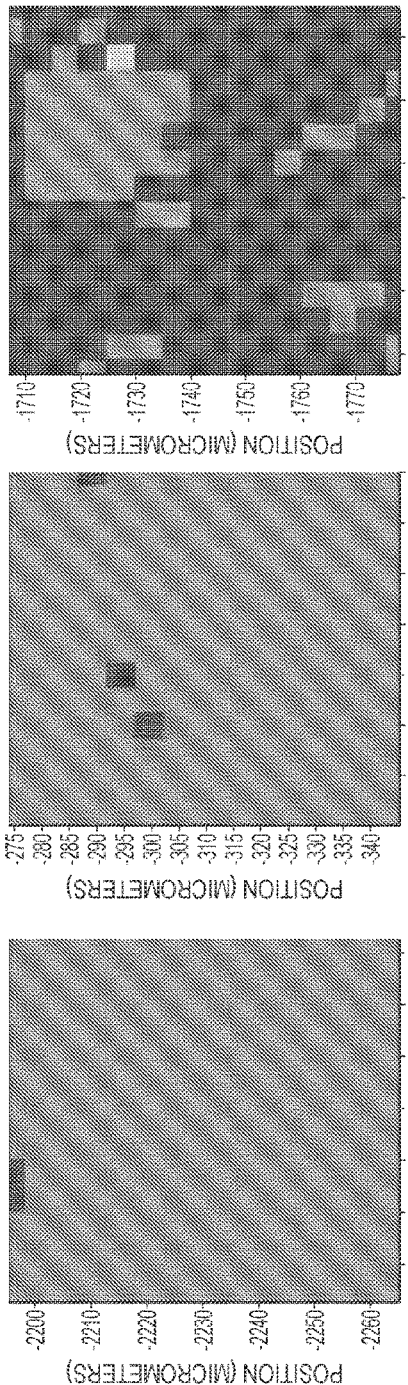
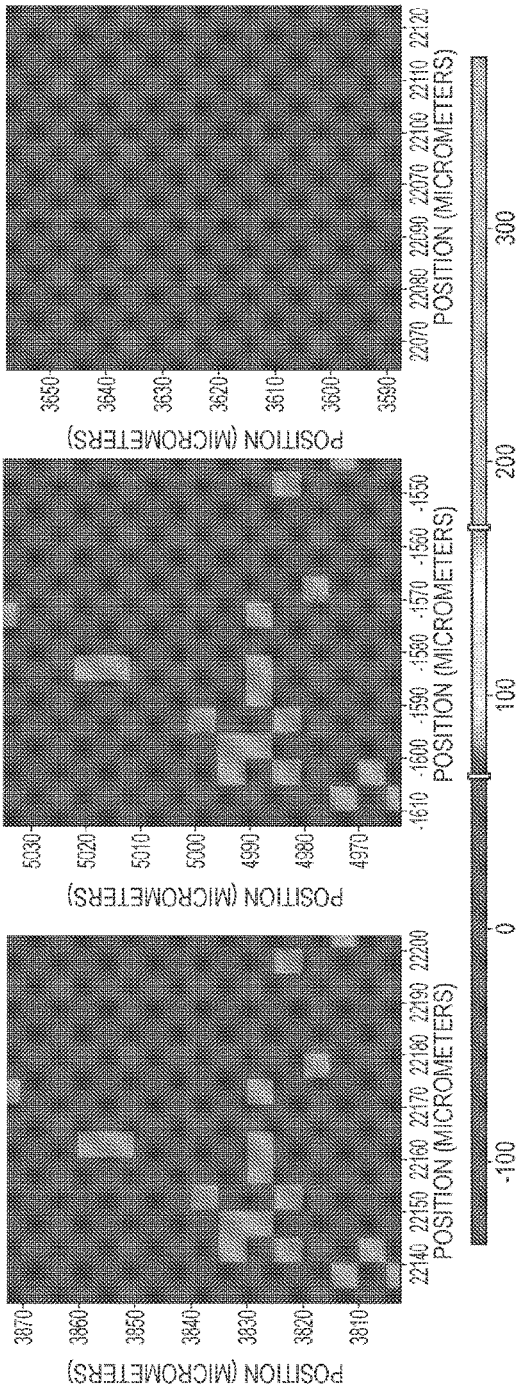
FIG. 7A  FIG. 7B  FIG. 7C
FIG. 7D  FIG. 7E  FIG. 7F

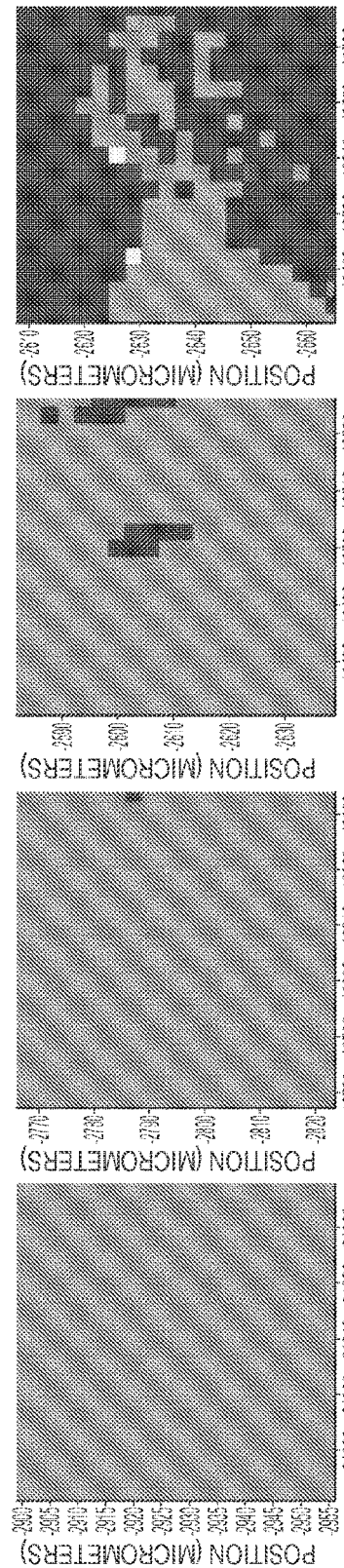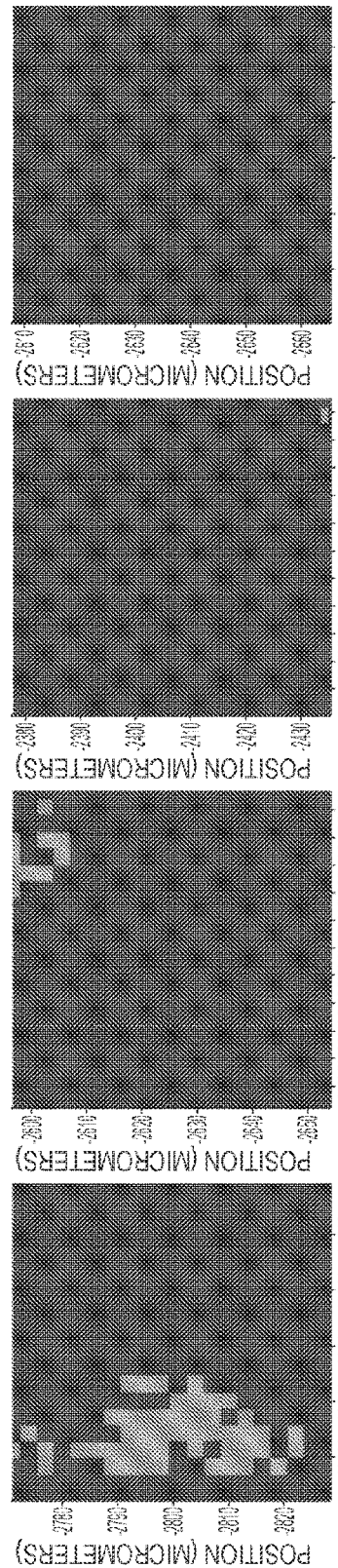
FIG. 14A   FIG. 14B   FIG. 14C   FIG. 14D
FIG. 14E   FIG. 14F   FIG. 14G   FIG. 14H

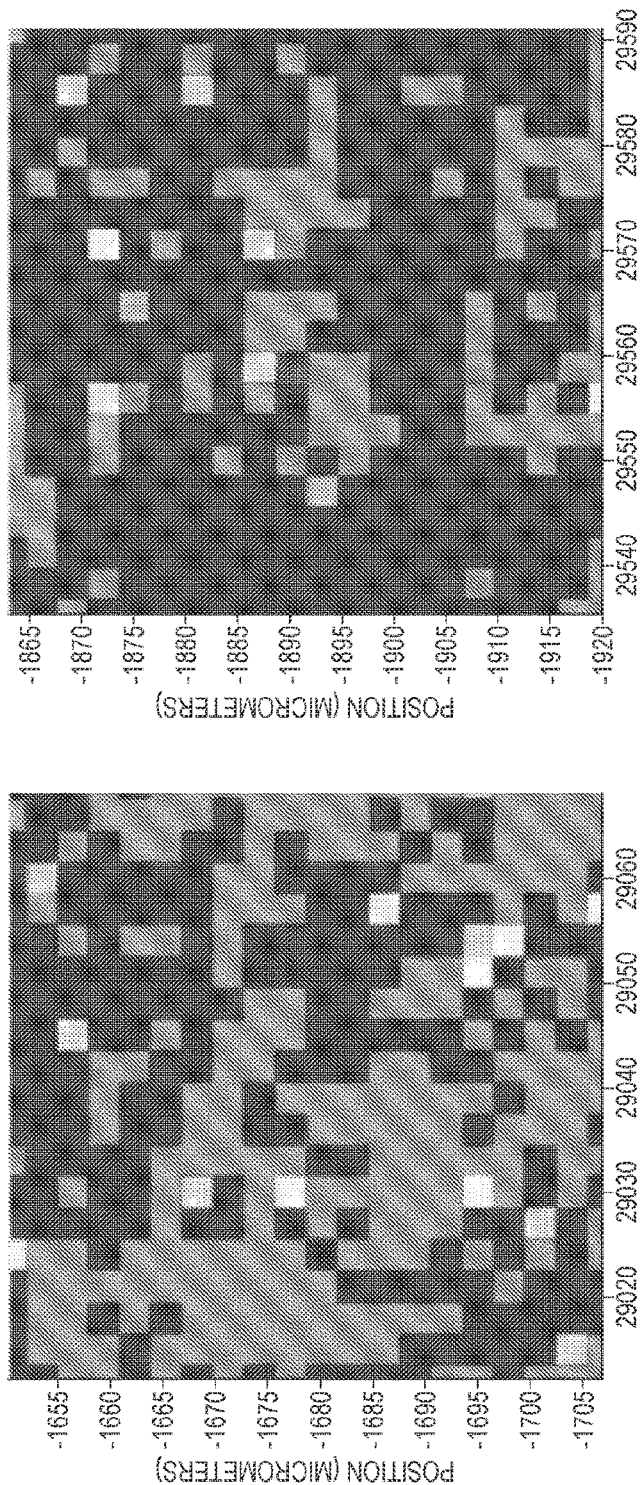

BACTERIAL DETECTION PLATFORM BASED ON SERS MAPPING

CROSS-REFERENCE TO RELATED APPLICATIONS

This application claims priority to and benefit of U.S. Provisional Application No. 62/171,010, filed Jun. 4, 2015, entitled BACTERIAL DETECTION PLATFORM BASED ON SERS MAPPING, and U.S. Provisional Application No. 62/170,381, filed Jun. 3, 2015, entitled FUNCTIONALIZED SERS-ACTIVE SYRINGE FILTRATION SYSTEM, both of which are incorporated by reference herein in their entirety for all purposes.

STATEMENT REGARDING FEDERALLY SPONSORED RESEARCH OR DEVELOPMENT

This invention was made with U.S. Government support from the USDA and NIFA under grants USDA-NIFA 2015-67021-22993 and USDA-NIFA hatch (MAS00491). The U.S. Government has certain rights to the invention.

BACKGROUND

These teachings relate generally to a bacterial detection platform based on Surface enhanced Raman scattering (SERS).

Illness and death due to pathogen-contaminated food supplies are on the rise, fueling concerns over safety of the nation's food supplies and the public's health, and leading to huge economic losses. According to the Centers for Disease Control and Prevention (CDC), in 2011, 31 major pathogens acquired in the United States caused upwards of 9.4 million episodes of foodborne illness, 55,961 hospitalizations, and 1,351 deaths.[1] In 2005, the Food and Drug Administration (FDA) estimated that the costs of foodborne illness ranged between \$10-\$83 billion annually.[2] Food pathogens such as *Salmonella enterica* and *Listeria* monocytogenes are "zero tolerated" in certain types of food products (e.g. "ready-to-eat" meats and dairy products, ground beef). Current food pathogen detection platforms, such as plating, polymerase chain reaction (PCR), and enzyme-linked immunosorbent assay (ELISA) require a significant step for cell enrichment, which is time consuming. Many of the rapid detection methods can't differentiate between live and dead cells, which may give an inaccurate estimation of the cells in the thermo processed food. A rapid, sensitive and accurate detection platform to detect bacteria cells in food matrices is essential to evaluate food contamination before the food products enter the supply chain.

Raman spectroscopy studies the molecular vibrations by light scattering, in which incident laser light is inelastically scattered from a sample and the wavelength of this light shifted in a manner of characteristic molecular vibrations. Placement of the sample of interest on noble metal nanoscale-roughened surfaces (typically silver or gold) tremendously enhances the inherently weak Raman molecular signatures, because of the large electromagnetic field induced by the excitation of the localized surface plasmon resonance (LSPR). This technique is so called surface enhanced Raman spectroscopy (SERS). Various SERS substrates have been fabricated and tested for bacteria. SERS detection capability is sensitive to the single bacterial cell/spore level. The capacity of SERS to discriminate pure bacterial sample is usually to species or even strain level with chemomatrics, such as principle component analysis (PCA) or hierarchical cluster analysis. The capabilities of using Ag dendrites in substrates for SERS have been greatly limited to detect bacterial cells in simple matrices.

There is a need for methods to separate bacteria from the matrices and concentrate the bacterial cells onto the SERS substrate. In addition, there is a need to discriminate between different species in a bacterial mixture.

There is a need for methods Ag dendrites in substrates for SERS for detecting bacteria in bacterial mixtures or in complex matrices.

Raman mapping technique is an advanced data collection technique for generating detailed chemical images based on a sample's Raman spectrum. A Raman spectrum is acquired at each and every pixel of the image, and then interrogated to generate artificial color images based on molecular composition and structure. A typical experiment uses sequential sample movement and spectrum acquisition to collect data from the user defined image area. This technique has been used widely in the characterization of eukaryotic cells and provides detailed information about the molecular composition of the subcellular volume being probed. The resolution of each pixel is usually about 0.5 to 3 µm, depending on the specific instrument Many of the current SERS detection studies of bacterial cells in complex matrices are based on secondary labeling with a Raman reporter. However, the Raman reporter—modified nanoprobe provides only the signature of the reporters and tends to be an imaging tool rather than a detection probe. The intrinsic bacterial cell information is missing; therefore Raman reporter based SERS method can't be used for differentiation between dead and live cells. In addition, the use of a secondary label significantly increases analytical time.

There is a need for label-free SERS methods for detecting bacteria.

SUMMARY

Label-free SERS methods for detecting bacteria in bacterial mixtures and in complex matrices, methods to separate bacteria from the matrices and concentrate the bacterial cells onto the SERS substrate are disclosed hereinbelow.

Raman mapping is applied, in the present teachings, for mapping mixed bacterial cells on a SERS-active substrate. The spectrum of each bacterial cell (for example, ~1 µm×~2 µm) can be acquired individually. Hundreds of spectra can be collected automatically in an array and a map generated for statistical analysis. Therefore, it is possible to identify and quantify each single bacterial cell in a mixture. To the best of our knowledge, there is no study using the Raman mapping technique to identify and quantify a mixed bacterial sample on a SERS-active substrate. With an advanced Raman microscope, hundreds of spectra can be collected simultaneously, which will generate a map of cells on the substrate in a few seconds.

For a better understanding of the present teachings, together with other and further needs thereof, reference is made to the accompanying drawings and detailed description.

BRIEF DESCRIPTION OF THE DRAWINGS

FIGS. 7a-7f shows SERS mapping data for an exemplary embodiment of these teachings;

FIG. 9b shows a summary of the identification results for the mapping data of FIG. 9a;

FIG. 14a-14h show SERS mapping data for another exemplary embodiment of these teachings at different concentrations in 1% casein using 4-MPBA coated Ag dendrites as substrates; and FIGS. 15a-15b show SERS mapping data for another exemplary embodiment of these teachings at different concentrations in skimmed milk using 4-MPBA coated Ag dendrites as substrates.

DETAILED DESCRIPTION

The following detailed description presents the currently contemplated modes of carrying out the invention. The description is not to be taken in a limiting sense, but is made merely for the purpose of illustrating the general principles of the teachings, since the scope of the teachings is best defined by the appended claims.

As used herein, the singular forms "a," "an," and "the" include the plural reference unless the context clearly dictates otherwise.

Figure 1:
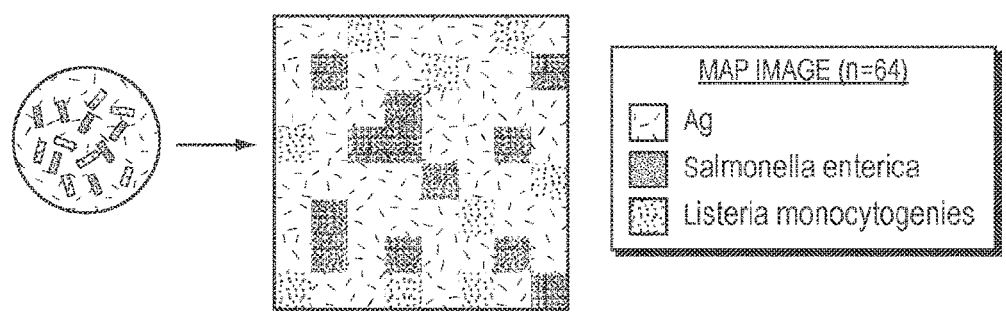
FIG. 1 is an illustration of detection and discrimination of a bacterial mixture on Ag substrate using the SERS mapping technique.

Described herein is a bacterial detection platform integrating the sensitive SERS technique and the advanced mapping technique. Basically, bacterial cells on the SERS substrate can be detected using the mapping technique. The identification is based on the fingerprint of the bacterial SERS spectra. The quantification of the cells will be based on the mapping technique (FIG. 1).

In one or more embodiments, the method of these teachings, based on label free surface enhanced Raman scattering (SERS) mapping, for detecting bacteria in bacterial mixtures includes capturing bacterial cells on a SERS substrate, capturing bacterial cells on a SERS substrate, collecting, using a Raman microscope, a number of spectra at each pixel in a defined area (the optical detector in the Raman microscope used in these teachings is are pixellated detector such as a CCD), generating a false color map of predetermined spectral regions and detecting the bacteria from the false color map. In one instance, the SERS substrate has nanostructures, the nanostructures being one of silver nanoparticles, gold nanoparticles or silver dendrites. In one embodiment, the nanostructures are functionalized with a bacterial capturers.

When applying the SERS techniques in complex matrices, like milk and ground beef, separation or concentration of the target bacteria from the matrix prior to spectral acquisition is critical to minimize the interference from food components. This is achieved by the use of bacterial capturers to concentrate the cells ahead of SERS spectral acquisition. There are two types of bacterial capturers, selective and nonselective.

Selective capturers: antibodies and aptamers are two major selective capture agents. Various commercial monoclonal and polyclonal antibodies are available. Nucleic acid aptamers are selectively engineered single-stranded DNA or RNA that can bind to a specific target molecule. They are relatively easy to create and manipulate, and often offer more stability, as well as improved sensitivity and robustness compared to antibodies. There are several published aptamer sequences for specific food pathogens. (See, for example, McKeague, M., Giamberardino, A., and DeRosa, M. C. (2011) Advanceds in aptamer-based biosensor for food safety, in Environmental biosensors (Somerset, V., Ed.), pp 17-42, which is incorporated by reference incorporated by reference herein in its entirety and for all purposes.)

Nonselective capturers: include certain antibiotics and antimicrobial peptides. They can specifically recognize and target certain molecules on the bacterial cell membrane. For example, vancomycin can bind Gram positive bacteria via hydrogen bonds between the peptidoglycan on the bacterial cell wall and the carbonyl and amine groups of vancomycin. Interestingly, it can also bind to Gram negative bacteria due to either unspecific binding between receptors on the pathogen surface and the glycosides on the vancomycin moiety or breaks/deformities in the outer membrane of the Gram-negative bacteria exposing D-alanyl-D-alanine groups on the interior bacterial surface. Particularly, vancomycin coated Ag array has been proved to capture and detect *Lactobacillus plantarum, Escherichia coli*, and *Enterococcus faecails* in blood samples using SERS. Theoretically, other glycopeptide antibiotics, such as teicoplanin, telavancin, bleomycin, ramoplanin, and decaplanin will have the similar capture capacity. A wide range of bacterial capturers within the scope of these teachings.

Figure 4:
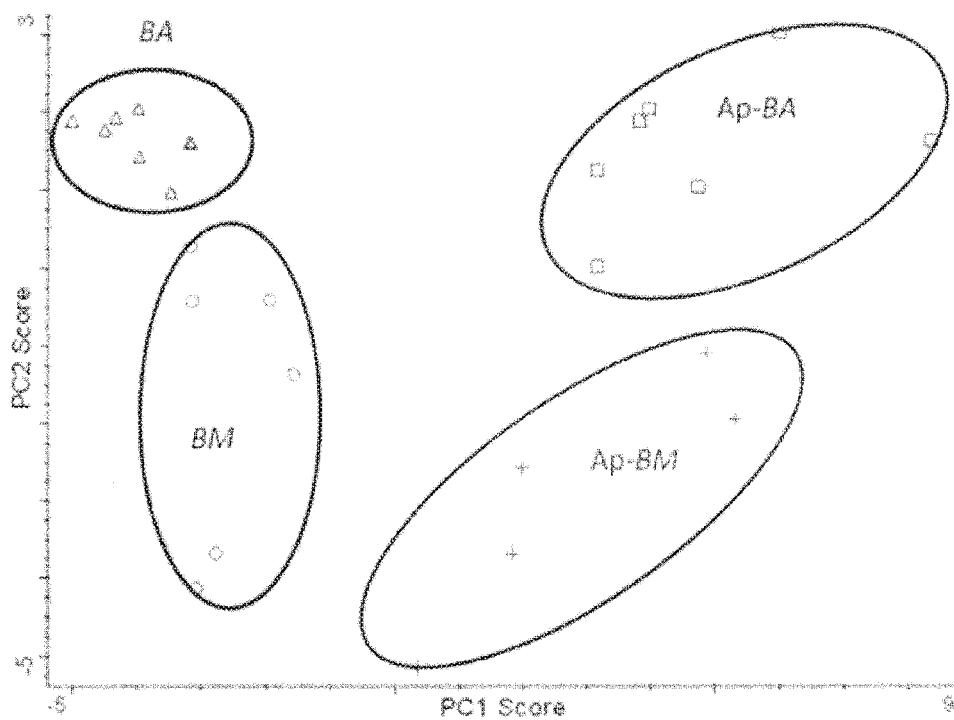
FIG. 4 is a PCA plot of SERS spectra of spores of *B. anthracis* (BA) and *B. mycoides* (BM) directly deposited on Ag, and captured by aptamer-conjugated Ag (ap-BA and ap-BM)
Figure 5:
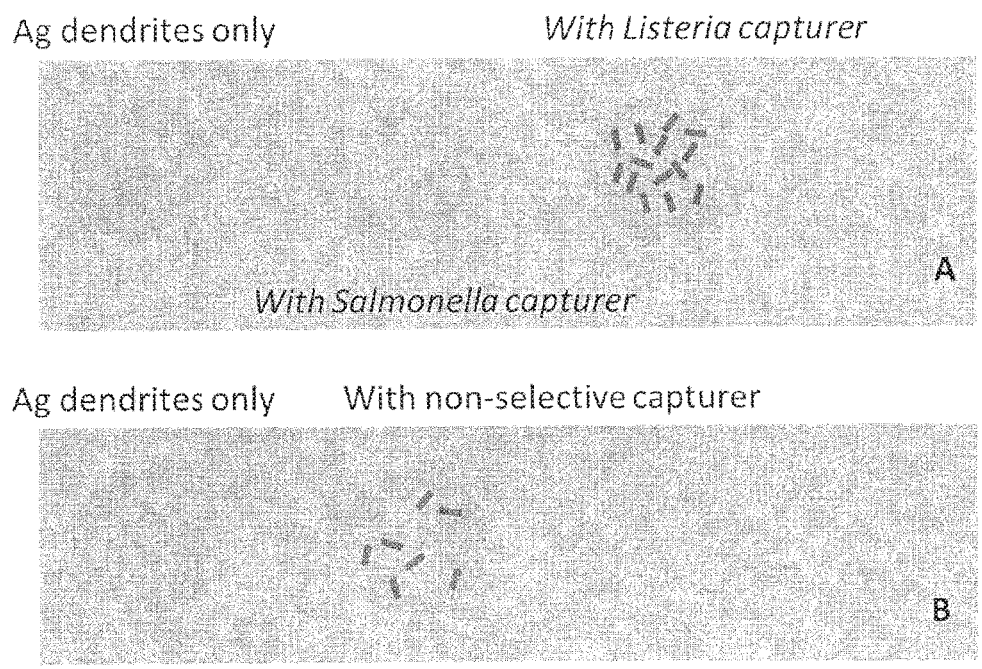
FIGS. 5a, 5b show SERS slides functionalized with selective capturers (A) and nonselective capturer (B)

To apply this SERS mapping technique in complex matrices, it is important to capture and concentrate the targets from the matrix. This can be achieved by conjugating capturers like antibody or aptamer onto the SERS substrates. One advantage of the label-free detection method of these teachings over other detection methods (e.g. the use of dye molecules as Raman reporter) is its high accuracy, which is based on the "finger-print" pattern of the target. Checking specific peak shifts and intensity allows confirmation that the captured target is, indeed, the one wanted to capture and detect. The aptamer is not specific, i.e. an aptamer can capture spores of *B. mycoides*, too, nevertheless, because the "fingerprint" of *B. anthracis* and *B. mycoides* are different, it was able to discriminate between them after they were captured, as illustrated in the PCA plot (FIG. 4). This is an advantage of the label-free SERS method of these teachings, compared with the reporter-based SERS method, which cannot differentiate two spores in this case.

Embodiments in which the nanostructures are nanoparticles, where the nanoparticles are filtered onto a membrane and embodiments in which the nanostructures are silver dendrites are disclosed hereinbelow.

Embodiments in Which Nanoparticles are Filtered Onto a Membrane

Figure 2:
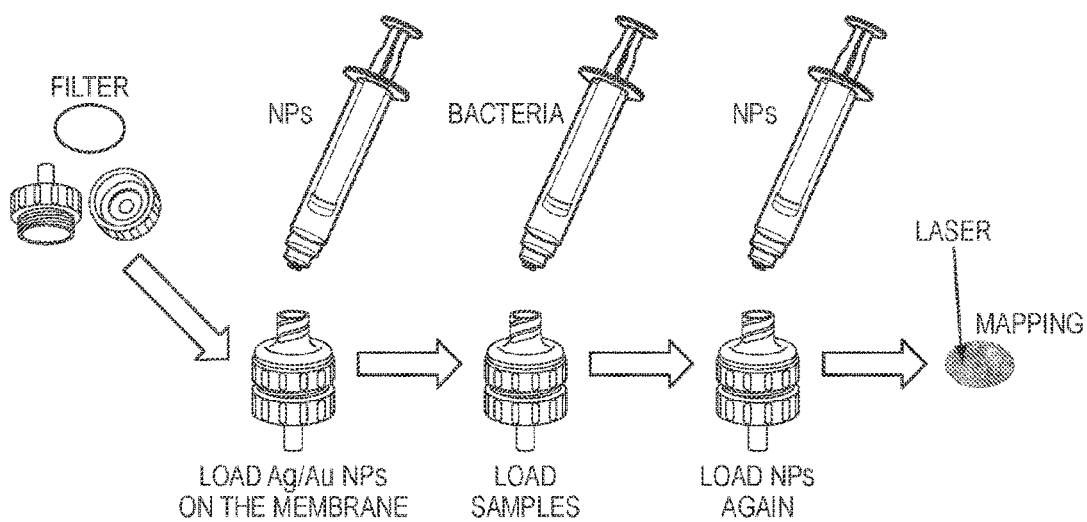
FIG. 2 is an illustration of using a syringe based filter membrane to concentrate the bacterial cells in water onto the SERS substrate for detection.

1. Concentration and Detection of Bacterial Cells in Water Using SERS Active Filter Membranes Membrane filtration techniques (FIG. 2) have been used for concentrating bacterial cells from water in food and pharmaceutical industry. Then the membrane can be put on top of bacterial culturing media to grow the cells. The growing and identification takes several days or over a week. Here the SERS substrate (silver and/or gold colloids: 0.2 mL to 25 mL; 10 ppm to 100 ppm; 30 to 150 nm) is integrated onto the filtration membrane (any bacterial filtration membrane is applicable) before following water through membrane. Bacterial cells are trapped onto the SERS active membrane during water filtration. In one instance, to enhance the detection sensitivity, another shot of silver or gold colloids are loaded after water filtration, so that the bacterial cells are sandwiched between the nanoparticles to maximize the sensitivity. The membrane can be taken out and air-dried. After that, the surface of membrane is scanned using Raman mapping (the mapping parameters are dependent on the Raman instrument). The detection and identification of bacterial cells are based on the enhanced bacterial characteristic signals. Using this invention, bacterial cells can be detected on the filter membrane within 4-8 hours depending on the size of membrane.

Figure 3:
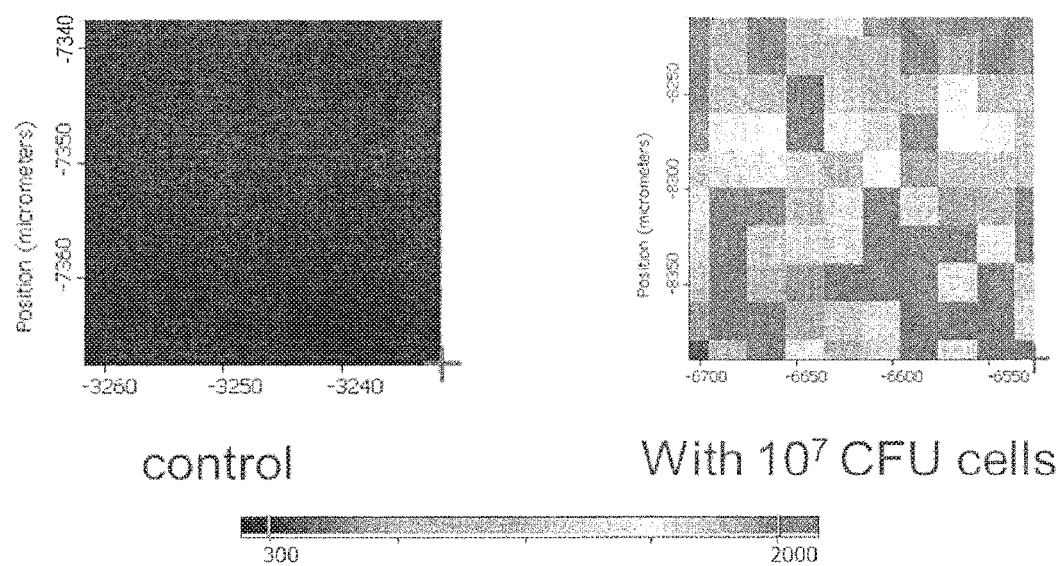
FIG. 3 shows a SERS image of bacterial cells on the SERS active filter membrane.

FIG. 3 is an example of mapping $10^7$ cfu/mL *Salmonella* cells in water on the filter membrane. The control without cells (just silver nanoparticles) has no/very low signals, so that the image is blue (indicating no/very low signals). With trapped cells, hot spots can be observed which indicate the cell signals. In the future study, lower concentrations of bacterial cells and a mixture of bacterial cells will be tested to evaluate the limit of detection and identification and quantification capacity.

Embodiments Using Silver Dendrites

One procedure for the preparation of the silver dendrites is presented herein below. Ag dendrites were prepared using a previously published zinc replacement method (see, He L, Lin M, Li H, Kim N J (2010) Surface-enhanced Raman spectroscopy coupled with dendritic silver nanosubstrate for detection of restricted antibiotics. J Raman Spectrosc 41:739-744). Briefly, 200 mM $AgNO_3$ solution was prepared by dissolving $AgNO_3$ (available at Fisher Scientific, Rochester, N.Y., USA) in double distilled water. The zinc plate (available at Fisher Scientific, Rochester, N.Y., USA) was cleaned with 20 mM hydrochloric acid solution and rinsed with double distilled water. After drying with air, the zinc plate was immediately immersed into the $AgNO_3$ solution for exactly 60 s. The Ag dendrites formed on the zinc surface were gently peeled off with a clean glass rod and washed with double distilled water several times.

In one instance, the silver dendrites are mounted on a solid support (for example, a slide). In the embodiment in which the solid support is a slide, in one instance, capturing bacterial cells includes fixedly placing the slides in a vessel, adding a liquid sample to the vessel, the liquid sample comprising the bacterial mixture, moving the vessel in order to makes the liquid sample and the slides, and, after a predetermined incubation period, drying the slides. In one instance, the method also includes removing excess liquid sample before drying the slides.

In another embodiment, capturing bacterial cells includes mixing the silver dendrites with a liquid sample, the liquid sample comprising the bacterial mixture, removing, after incubation, excess liquid sample, placing the silver dendrites on a solid support and drying the solid support on which the silver dendrites are placed.

Concentration and Detection of Bacterial Cells from Complex Matrices Using SERS Substrate Contained Vessel Different strategies can be used to conjugate different capturers on to SERS substrates. Aptamers will be thiolated first and incubated overnight with Ag dendrites to form a strong thiol-Ag/Au bond like previous described. For antibodies, a protein G will be first conjugated onto nanosubstrates by electrostatic interaction, then the protein G will bind the antibodies.[27] Antibiotics and short peptides are easily adsorbed onto Ag surface by incubating them overnight.

Figure 6:
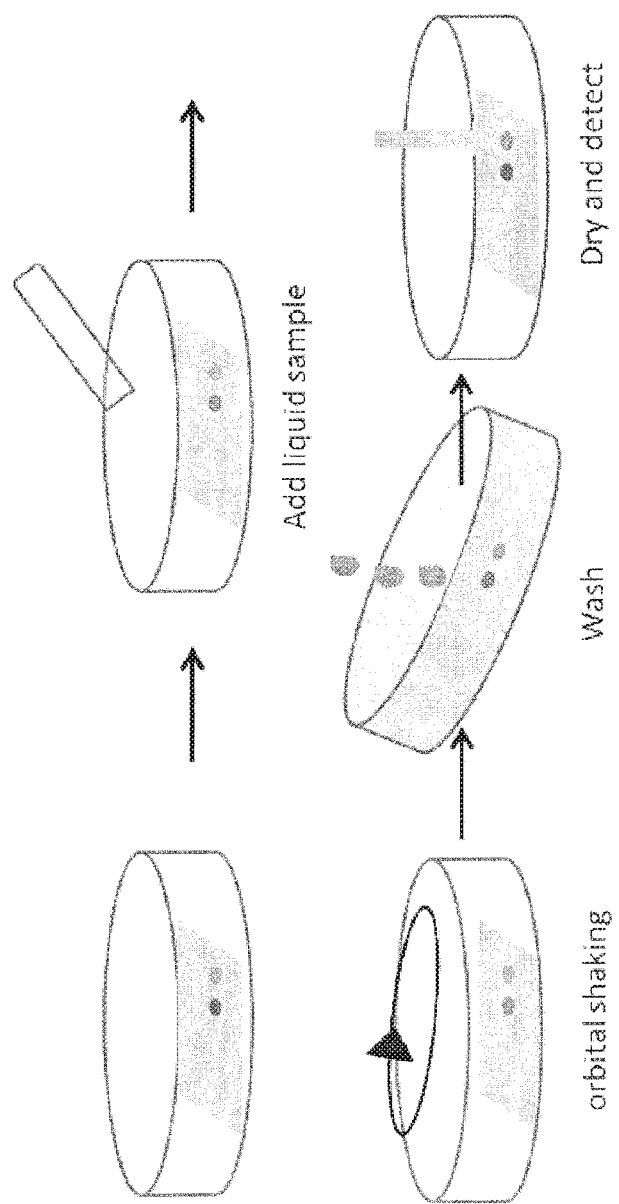
FIG. 6 is an illustration of a method of these teachings of using the SERS substrate contained vessel to concentrate and detect mixed bacteria from a complex liquid matrix.

Depending on the specific application, the slide can be designed with multiple spots of SERS substrate with selective capturers (FIG. 6A), or the slide with Ag dendrites with a nonselective capturer (FIG. 6B). Each capturer-modified SERS substrate will be prepared individually and mounted on a solid support (e.g. standard microscopic slide). A slide with multiple capturers can be read and analyzed automatically using SERS mapping.

The general procedure of the detection platform is described in FIG. 7: 1) slides will be fixed in a vessel (e.g. petri-dish), 2) add liquid sample, 3) place the vessel on a shaker for gentle orbital shaking for 15-30 min, 4) wash it using water several times to wash away any bacterial cells with non-specific association, and 5) dry the slide in a hood and put it in the Raman instrument for SERS mapping.

This design is selected for capture since it can hold 30-40 mL of liquid sample provides a sufficient sampling for detecting bacteria cells. This format also provides the ease of orbital shaking, which allows larger volumes of liquid to be exposed to SERS substrates containing the capturers. After removal of liquid, the slide can placed under the Raman microscope, without removing the vessel, which adds a protection for microbial containment within the instrument.

In order to elucidate these teachings, exemplary embodiments are presented hereinbelow. It should be noted that these exemplary embodiments do not limit the scope of these teachings. Other embodiments are within the scope of these teachings.

Label-Free Mapping of Single Bacterial Cells

In this exemplary embodiment, the SERS mapping method of these teachings is used for directly scanning single bacterial cells on the surface of Ag dendrites for the detection of *Salmonella*, and simultaneous detection and identification of a bacterial mixture containing *Salmonella* and *Escherichia coli* (*E. coli*). *Salmonella* is a major foodborne pathogen for both humans and animals. It widely exists in many kinds of food and can disseminate through raw and undercooked food. The incidence of foodborne infections caused by *Salmonella* continues to be an important problem in many countries. (See Label-free mapping of single bacterial cells using surface-enhanced Raman spectroscopy, *Analyst*, 2016, 141, 1356, which is incorporated by reference herein in its entirety and for all purposes.)

*Salmonella enterica* subsp. *enterica* BAA1045 (SE1045) and *E. coli* BL21 were used in this exemplary embodiment. Frozen cultures of the bacteria were revived in tryptone soy agar. Fresh bacteria culture was prepared by transferring a single colony into 10 mL tryptone soy broth and cultivated at 37° C. for approxi-mately 12 h. Bacterial cells were collected by centrifugation at 5000 g for 5 min. The collected bacteria cells were washed with 10 mM phosphate-buffered saline (1×PBS, pH 7.4) three times and re-suspended in 10 mM PBS unless otherwise stated. Before SERS measurements, the washed bacterial cultures were serially diluted in 10 mM PBS. *E. coli* BL21, *Listeria* monocytogenes 18 (LM18) and *Lactococcus lactis* (*L. lactis*) LM0230, were prepared in a similar manner.

For SERS measurements, 20 µL prepared bacterial suspension was mixed with 6 µL Ag dendrites on a piece of parafilm and pipetted in-and-out for about 20 s. The mixture was then dropped onto a hydrophobic glass slide. After drying in the biosafety cabinet, SERS spectra were collected directly from the sample spots using a DXR Raman spectromicroscope (Thermo Scientic, Madison, Wis.). All measurements were conducted using a 10× microscope objective, 780 nm excitation wavelength, 5 mW laser power and 50 µm slit aperture for 2 s integration time. For the label-free SERS mapping method, a 75 µm×75 µm mapping area was randomly selected and the mapping data were collected with a step size of 5 µm. The selected area contains 225 data points which should be statistically presentative for the bacterial sample. The larger the area, the more information we may get, however, this would also increase the analytical time. To scan such an area, it takes around 24 min for the current instrumentation which is based on point by point scanning. SERS spectra were analyzed with TQ Analyst software (version 8.0) developed by Thermo Scientific. OMNIC™ software version 9.1 was used to control the Raman instrument.

Water, saline and PBS are the three most commonly used suspending solution for SERS-based methods to analyze bacterial samples. PBS was used in this exemplary embodiment. The concentration of PBS was optimized to maximize the signal intensity. 10 mM was the optimal PBS concentration used. The ratio of Ag dendrites and the bacteria suspension was also optimized. 6 µL of Ag dendrites is the appropriate volume for 20 µL of bacterial suspension, giving the highest peak intensity of almost 7000 A.U. at ~1330 $cm^{-1}$.

The limit of detection (LOD) of the label-free SERS mapping method was then determined under the same experimental condition. A 75 µm×75 µm mapping area was randomly selected and the mapping data were collected with a step size of 5 µm (containing 225 data points). The SERS image was constructed based on the intensity of the 1332 $cm^{-1}$ (FIG. 7). The positive detection was defined when the intensity at 1332 $cm^{-1}$ is higher than the value of average intensity of the background spectra plus three times the standard deviation of the background spectra. FIGS. 7*a*-7*f* show SERS mapping data of SE1045 at different concentrations of (a) $2.1 \times 10^8$ CFU $mL^{-1}$, (b) $2.1 \times 10^7$ CFU $mL^{-1}$, (c) $2.1 \times 10^6$ CFU $mL^{-1}$, (d) $2.1 \times 10^5$ CFU $mL^{-1}$, (e) $2.1 \times 10^4$ CFU $mL^{-1}$, (f) control. Mapping data were created based on the vibrational mode of ~ at 1332 $cm^{-1}$. Red (lighter): SE1045; blue: Ag dendrites. The red spots in the image represent the intensity higher than 176 A.U., which indicates the detection of bacterial signals. The blue (darker) spots represent the intensity lower than 69 A.U., which means no bacterial signal was observed. At high concentrations (i.e. $2.1 \times 10^8$ and $2.1 \times 10^7$ CFU $mL^{-1}$), red (lighter) spots were detected all over the scanned area, which indicates the full coverage of the bacterial cells on the Ag dendrites. The number of the red spots decreased as the concentration of the bacteria decreased, and the LOD of the SERS-mapping method was as low as $10^4$ CFU $mL^{-1}$. The time needed for a 75 µm×75 µm mapping area containing 225 data spots was approximately 24 min.

Figure 8:
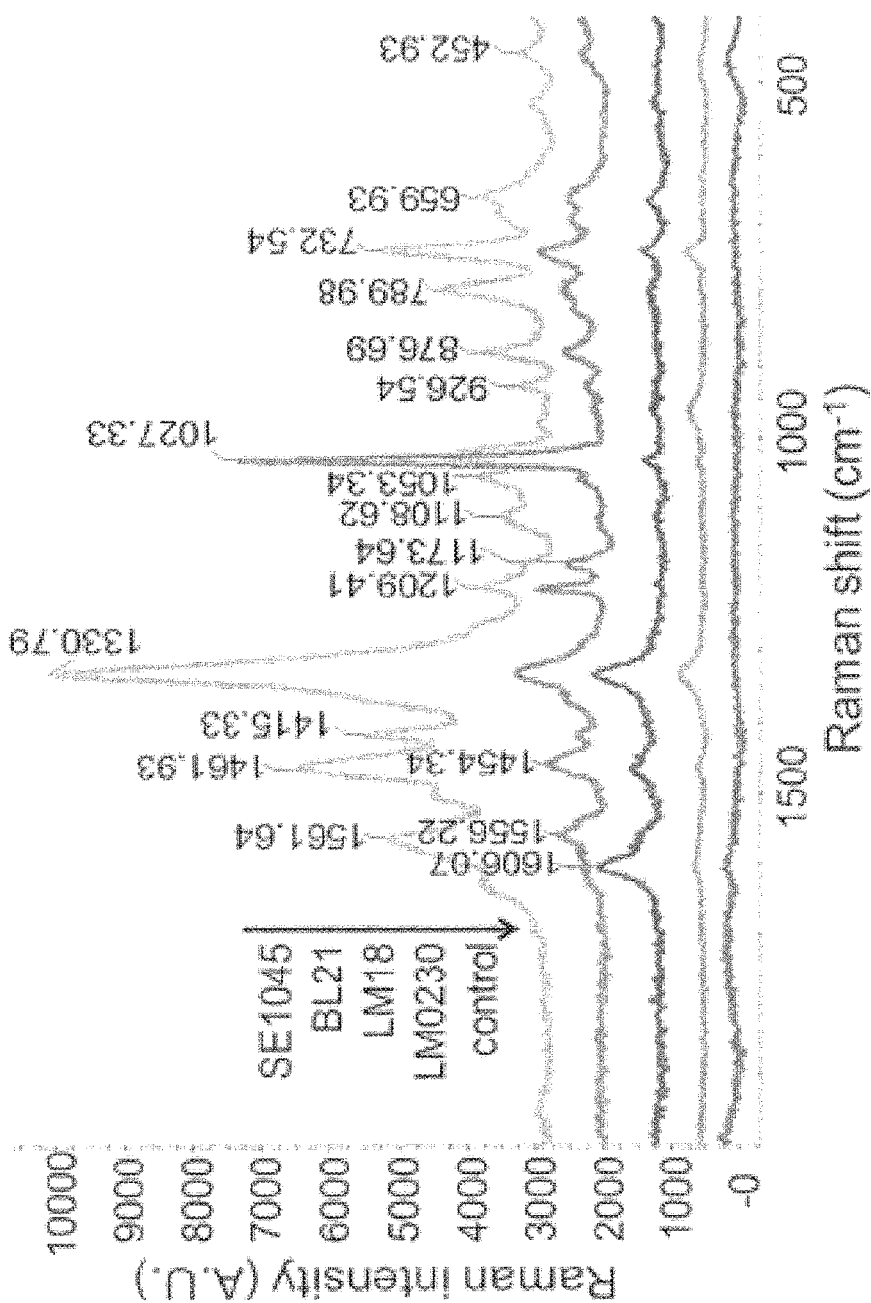
FIG. 8 shows SERS spectra of different strains using Ag dendrites as substrates for an exemplary embodiment of these teachings.
Figure 9A:
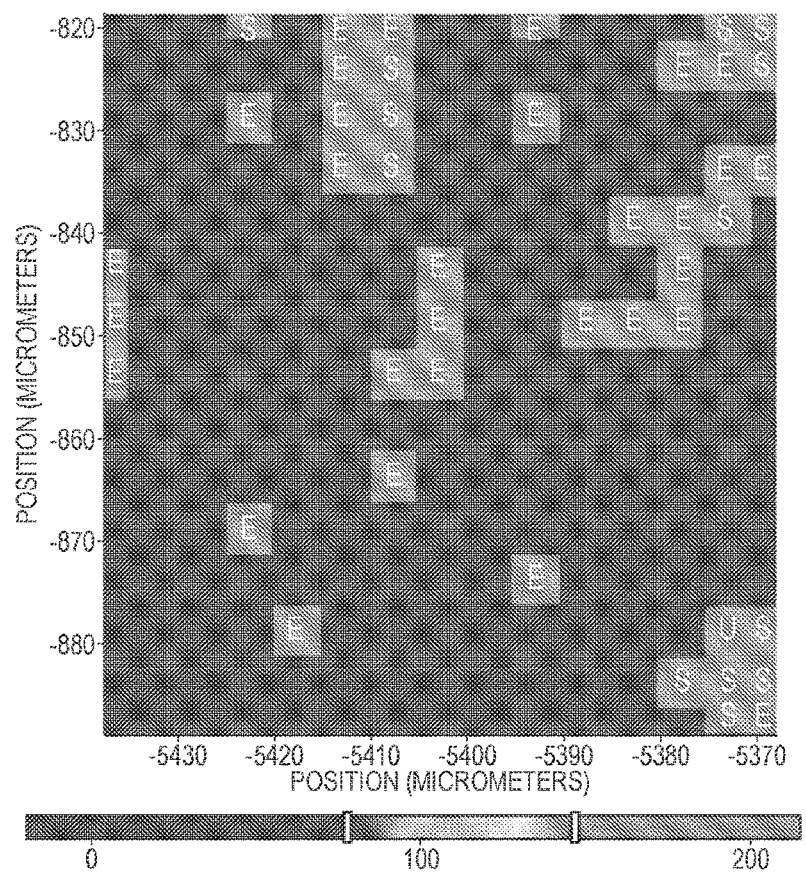
FIG. 9a shows SERS mapping data for an exemplary embodiment of these teachings.
Figure 9B:
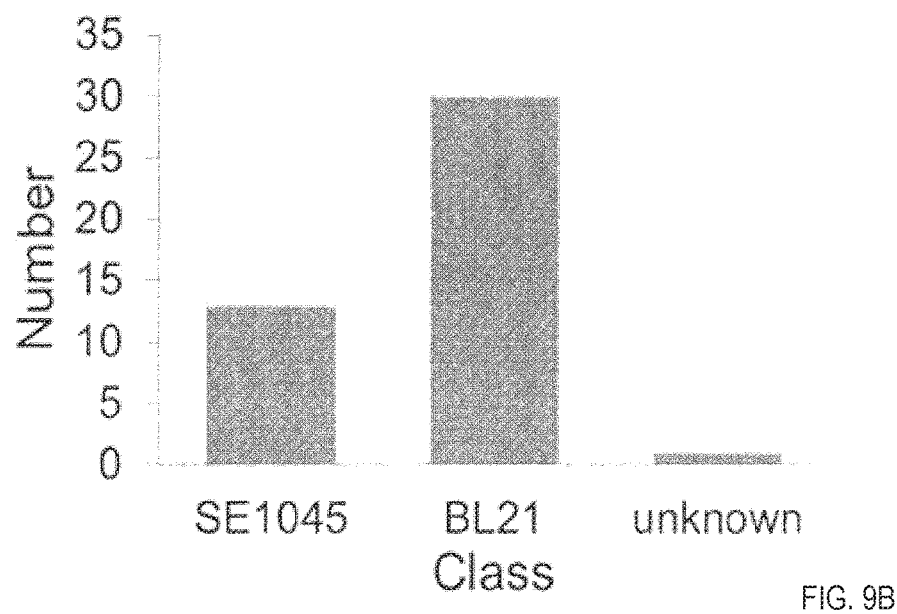

The efficiency of the Ag dendrites assisted label-free SERS method to discriminate different bacteria was evaluated using two Gram negative (G−) and two Gram positive (G+) strains. As can be seen from FIG. 8, Ag dendrites made in this study have a better enhancement for the Gram negative strains than the Gram positive strains. Although the spectra of both the Gram negative and Gram positive strains showed clear peaks at around 1330 and 732 $cm^{-1}$, the patterns of spectrum of the four strains were different, making the correct identification of a specific strain feasible. A prediction model based on the spectra of SE1045 and *E. coli* BL21 was built for the detection and identification of their mixture sample. Principal component analysis (PCA) was used to check the statistical difference between the two Gram negative strains and used as a prediction model. The PCA plot showing the spectra of SE1045, *E. coli* BL21 and Ag dendrites (control) can be clearly distinguished, which indicates the prediction model has a good quality (FIG. 9(*b*)). Mapping data of a bacterial mixture containing SE1045 and *E. coli* BL21 (106 CFU mL-1, 1 to 1) were collected (FIG. 9(*a*)). (In FIG. 9*a*, S: SE1045; E: *E. coli* BL21; U: unknown (failed to identify); blue (darker): Ag dendrites.) The mapping data were generated based on the peak intensity at ~1330 cm-1. A positive detection was spotted when the intensity was higher than the value of average intensity of the spectra collected from Ag dendrites plus three times the standard deviation of the obtained Ag dendrites spectra. Based on this definition, 44 sample spots were detected.

Rapid Concentration Detection and Differentiation of Bacteria in Skimmed Milk

In this exemplary embodiment, a small nonselective bacterial capture, 4-mercaptophenylboronic acid (4-MPBA), was functionalized on Ag dendrites to enhance the sensitivity and specificity of the SERS mapping method of these teaching for the concentration, detection and differentiation of bacteria in liquid food (i.e. 1% casein and skimmed milk). 4-MPBA contains two functional groups, a thiol group that can strongly bind with Ag or Au and a boronic acid group that can binds with peptidoglycan in bacterial cell wall through the covalent bonds between boronic acid and cis-diol.

Preparation of the 4-MPBA Functionalized Ag Dendrites

Ag dendrites were prepared using a previously published zinc replacement method. Briefly, 200 mM AgNO3 solution was prepared by dissolving AgNO3 (available at Fisher Scientific, Rochester, N.Y., USA) in double distilled water. The zinc plate (available at Fisher Scientific, Rochester, N.Y., USA) was cleaned with 20 mM hydrochloric acid solution and rinsed with double distilled water. After drying with air, the zinc plate was immediately immersed into the AgNO3 solution for exactly 60 s. The Ag dendrites formed on the zinc surface were gently peeled off with a clean glass rod and washed with double distilled water several times. After washing, 100 µL of Ag dendrites were mixed with 1 mL 1×10−4 mM 4-MPBA ethanol solution and incubated for 12 h at room temperature unless otherwise stated. After incubation, the supernatant was discarded and the Ag dendrites were washed two times with ethanol. The ethanol residue was removed with airflow. After drying, 1 mL of 50 mM NH4HCO3 was added to the Ag dendrites. SERS spectra of the Ag dendrites were collected after each step Sample Preparation

*Salmonella enterica* subsp *enterica* BAA1045 (SE1045) was used to represent the pathogenic bacteria in this study. Frozen cultures of the SE1045 were revived in tryptone soy agar (TSA, Difco, Detroit, Mich.). Fresh bacteria culture was prepared by transferring a single colony into 10 mL of tryptone soy broth (TSB, Difco, Detroit, Mich.) and cultivated at 37° C. for approximately 12 h. Bacterial cells were collected by centrifugation at 5000 g for 5 min. The collected bacteria cells were washed with sterile double distilled water three times to remove the broth residue. *E. coli* BL21, *Listeria* monocytogenes 18 (LM18) and *Lactococcus lactis* (*L. lactis*) LM0230, were prepared in a similar manner. The detection limits of the developed method for *Salmonella* in different liquid samples were studied by suspending the washed cells in 50 mM $NH_4HCO_3$ solution, 1% casein digest solution, or commercial fat-free milk and the contaminated samples were serially diluted with 50 mM $NH_4HCO_3$ solution, 1% casein digest solution, and commercial fat-free milk, respectively. The SE1045 cells were incubated with 1% casein and skimmed milk for 1 h to better simulate the real situation. Before SERS measurements, 1 mL of each sample was centrifuged at 5000 g for 10 min, washed twice with an equal volume of sterile double distilled water, and re-suspended with 1 mL of 50 mM $NH_4HCO_3$ solution. The concentrations of the SE1045 suspension were detected by spreading 200 μL of the diluted suspension on TSA and the variation of the concentration before and after incubating with both the pristine and the 4-MPBA functionalized Ag dendrites were used to reflect the capture efficiency of these two substrates respectively.

SERS Measurements

For SERS measurements, 10 μL of 4-MPBA functionalized Ag dendrites was mixed with 1 mL of the prepared bacterial cells suspension and incubated for 30 min under gentle shaking (20 rpm/min) at room temperature to capture the bacterial cells unless otherwise stated. After incubation, the supernatant was removed with pipette and the Ag dendrites were washed twice with sterile double distilled water. After washing, the Ag dendrites were collected and dropped onto a hydrophobic glass slide and dried in the biosafety cabinet. After drying, SERS spectra were collected directly from the sample spots using a DXR Raman Spectromicroscope (Thermo Scientic, Madison, Wis.). All measurements were conducted using a 10× microscope objective, 780 nm excitation wavelength, 5 mW laser power and 50 μm slit aperture for 1 s integration time. For the SERS mapping method, a 60 μm×60 μm mapping area was randomly selected and the mapping data were collected with a step size of 3 μm. The selected area contains 400 data points and is statistically representative for the bacterial sample. It takes nearly 30 min for the current instrumentation that is based on point by point scanning to obtain such a mapping image. SERS spectra were analyzed with TQ Analyst software (version 8.0) developed by Thermo Scientific. OMNIC™ software version 9.1 was used to control the Raman instrument.

Results

Preparation of 4-MPBA Functionalized Ag Dendrites

Ag dendrites synthesized using the simple zinc replacement method were incubated with $1 \times 10^{-4}$ mM 4-MPBA for 12 h at room temperature, and then washed twice with ethanol. After washing, 50 mM $NH_4HCO_3$ solution was added to the 4-MPBA coated Ag dendrites and incubated for 3 min before use. SERS spectra of the Ag dendrites after each step were collected and depicted in FIG. 1. FIG. 1 shows the pristine Ag dendrites made in this manner give a peak at approximately 1070 cm$^{-1}$. This peak is attributed to the $NO_3^-$ residue in the substrate. Coating 4-MPBA onto Ag surface can reduce the background signal of Ag dendrites by more than 10 times. Interestingly, the 4-MPBA signals increased significantly (about 40 times) after contacting with $NH_4HCO_3$. And this intensity increase is not the overlap effects of the signals of 4-MPBA and $NH_4HCO_3$ since the two characteristic peaks of 4-MPBA around 1000 cm$^{-1}$ were also increased obviously. Moreover, the interference from $NH_4HCO_3$ is not affected by the concentration of the $NH_4HCO_3$. $NH_4HCO_3$ can significantly enhance the SERS signal of 4-MPBA. 4-MPBA contains two functional groups, a thiol group that can strongly bind with Ag or Au and a boronic acid group that can bind with peptidoglycan in bacterial cell wall through the covalent bonds between boronic acid and diol. $NH_4HCO_3$ was added because the reaction between boronic group and peptidoglycan is more favorable in basic solution. The exact mechanism for the great enhancement in the SERS signal of 4-MPBA caused by $NH_4HCO_3$ is currently unknown.

Optimizing the SERS Parameters

Experimental parameters were optimized to obtain high capture efficiency and SERS enhancement for pathogens detection. The concentration of 4-MPBA used to coat Ag dendrites, solutions used to suspend the bacteria cells, incubation time of the bacterial cells and 4-MPBA coated Ag dendrites as well as the laser exposure time for SERS spectra collection were optimized in this study. SERS spectra were randomly collected from each samples and the peak at around 740 cm$^{-1}$ was used as the characteristic peak of SE1045. The peak at 740 cm$^{-1}$ is mainly originated from the peptidoglycan in the cell wall. Difference of this peak intensity for the test sample and the control, $\Delta(T_{740}-C_{740})$, was used to compare the performance of different parameters.

Different concentrations of 4-MPBA were used to coat Ag dendrites. The optimal concentration was selected when the signals of SE1045 were not overwhelmed by the relatively strong SERS signals of 4-MPBA. The 1×10-4 mM 4-MPBA coated Ag dendrites give the highest absolute SE1045 intensity of approximately 1000 A.U., which was closely followed by the 1×10-3 mM 4-MPBA coated dendrites. However, when Ag dendrites were coated with 1×10-3 mM 4-MPBA, the signal of SE1045 probably blocked by the signal of 4-MPBA since no obviously peak at ~740 cm-1 was observed. Therefore, 1×10-4 mM 4-MPBA solution was used to construct the 4-MPBA functionalized Ag dendrites in the following experiment.

The reaction between boronic group and peptidoglycan is more favorable in basic solution than in distilled water. The constructed 4-MPBA functionalized Ag dendrites were used to capture SE1045 cells suspended in both sterile double distilled water and 50 mM $NH_4HCO_3$ solution (pH~9.0). The intensity at 740 cm$^{-1}$ is 3562 A.U. for SE1045 suspended in 50 mM $NH_4HCO_3$ solution is more than four times higher than that for the spectra collected from cells suspended in sterile double distilled water. 50 mM $NH_4HCO_3$ solution can enforce the boronic-diol interaction between 4-MPBA and bacterial cell wall as well as enhance the intensity of the bacterial peaks.

As for the time needed for the 4-MPBA functionalized Ag dendrites to capture SE1045 cells, no obvious difference was observed for different incubation times, illustrating that 30 min was enough for the 4-MPBA coated Ag dendrites to capture SE1045 cells. Hence, in the following experiments the 4-MPBA functionalized Ag dendrites was only incubated with the bacterial solution for 30 min.

Different sample exposure times, which were used for the Raman instrument to focus a selected sample spot before collecting the spectrum, were used to collect the spectra of SE1045 and the intensity of the characteristic peak of SE1045 at 740 cm-1 were compared to minimize the time needed for each sample spot. The detected bacterial signal at 740 cm-1 doesn't change with the variation of exposure time, making it an ideal substrate for the rapid mapping study.

Capture efficiency of the 4-MPBA functionalized and pristine Ag dendrites for SE1045 under the optimized conditions was tested using plate count colony method. However, the capture efficiency of the 4-MPBA functionalized Ag dendrites was more than two times higher than that of the pristine Ag dendrites at all the detected bacteria concentrations. The 4-MPBA functionalized Ag dendrites captured as many as 99.65±3.58% of the SE1045 cells at the concentration of 103 CFU/mL. And at the concentration of 106 CFU/mL the capture efficiency of the 4-MPBA functionalized Ag dendrites was still about 84.92±3.25%, while for the pristine Ag dendrites the capture efficiency was just about 22.04±2.13%. Therefore, anchoring 4-MPBA onto Ag dendrites can significantly increase its capture efficiency for SE1045, which is of critical importance for the accurate and sensitive detection of SE1045.

The LOD of the mapping method using 4-MPBA functionalized Ag dendrites as substrate was detected in different lipid samples. A 60 μm×60 μm mapping area was randomly selected and the mapping data were collected with a step size of 3 μm, resulting in 400 spectra per map. This was to ensure a statistical representative data was obtained for analysis. Increasing the map area may result in a more sensitive detection statistically, however, it also increases the scanning time. Herein, the scanning time was controlled within 30 min. Mapping images were constructed based on the intensity of the peptidoglycan peak at ~740 cm-1. The positive detection was defined when the intensity is higher than the value of average intensity of the background spectra plus three times of their standard deviation. The red spots in the image represent positive signals, indicating the detection of bacterial signals. The blue and green spots represent the negative detection, meaning no bacterial signal was observed.

In this exemplary embodiment, SERS mapping method was first used to detect SE1045 in 50 mM NH4HCO3. Red spots were observed almost all over the scanned area at high concentrations (i.e. 2.27×108 and 2.27×107 CFU/mL), which indicates the full coverage of the bacterial cells on Ag dendrites. The number of the red spots decreased sharply as the concentration of SE1045 decreased, and the LOD of the SERS mapping method was 103 CFU/mL. Compared with the exemplary embodiment using pristine Ag dendrites with a LOD of 104 CFU/mL, coating 4-MPBA onto Ag dendrites lowered the LOD of the mapping method by 10 times. More importantly the 4-MPBA functionalized Ag dendrites can specifically capture bacterial cells under the interference of components that don't react with boronic groups and thus it is very promising to be utilized for the detection of pathogens in food matrices.

Commercially available skimmed milk was used to represent the liquid food samples. Prior to detecting SE1045 in skimmed milk, the performance of the 4-MPBA functionalized Ag dendrites in 1% casein solution was examined. FIGS. 14*a*-14*g* shows the mapping results of SE1045 at different concentrations in 1% casein. Referring to FIGS. 14*a*-14*g*, the figures show mapping results of SE1045 at different concentrations in 1% casein using 4-MPBA coated Ag dendrites as substrates. (A) 2.27×10$^8$ CFU/mL; (B) 2.27×10$^7$ CFU/mL; (C) 2.27×10$^6$ CFU/mL; (D) 2.27×10$^5$ CFU/mL; (E) 2.27×10$^4$ CFU/mL; (F) 2.27×10$^3$ CFU/mL; (G) 2.27×10$^2$ CFU/mL; (H) control. Mapping data were created based on the vibrational mode of at 740 cm$^{-1}$; Red: SE1045; others: Ag dendrites. Similar with the results in the 50 mM NH4HCO3, positive signals were detected all over the scanned area for the high concentrations of SE1045 and decreased as the concentration of bacteria decreased. However, at low bacteria concentrations (105 to 103 CFU/mL) more positive signals were detected in 1% casein. Moreover, the LOD of the SERS mapping method using the same parameters was as low as 102 CFU/mL, which was ten times lower than that in 50 mM NH4HCO3. This is probably due to some subtle chemical or structure change happened when the bacterial cells were exposed to casein, and this kind of change can improve the interaction between the cell wall and the boronic group. It is really exciting that the interference of casein increases the sensitivity of 4-MPBA functionalized Ag dendrites for SE1045 rather than decreasing it.

In commercial fat-free milk, overnight-cultivated SE1045 cells were inoculated into skimmed milk intentionally and maintained in it for 1 hour and no obvious bacteria growth was observed during this period. Bacterial cells were recovered using low speed centrifugation and washed twice with sterile double distilled water. After capturing, the 4-MPBA functionalized Ag dendrites were gently washed two times with sterile double distilled water before collecting the SERS spectra. The mapping data were collected from the dried dendrites and results were given in FIG. 15*a*-15*b*. Referring to FIGS. 15*a*-14*b*, the figures show mapping results of SE1045 at different concentrations in skimmed milk using 4-MPBA coated Ag dendrites as substrates. (A) 2.27×10$^8$ CFU/mL; (B) 2.27×10$^7$ CFU/mL. Mapping data were created based on the vibrational mode of ~ at 740 cm$^{-1}$. Red (lighter gray): SE1045; others: Ag dendrites. It shows that the number of positive signals decreased with the decrease of bacteria concentration.

Embodiments of the Active Membrane Substrate

A SERS-active syringe filtration system that can be used for larger volumes of samples is presented here in. To enhance the selectivity and sensitivity, in another embodiment, capturers (e.g. aptamers) are also conjugated on the SERS-active membrane to selectively concentrate the target in the samples if needed.

Figure 10:
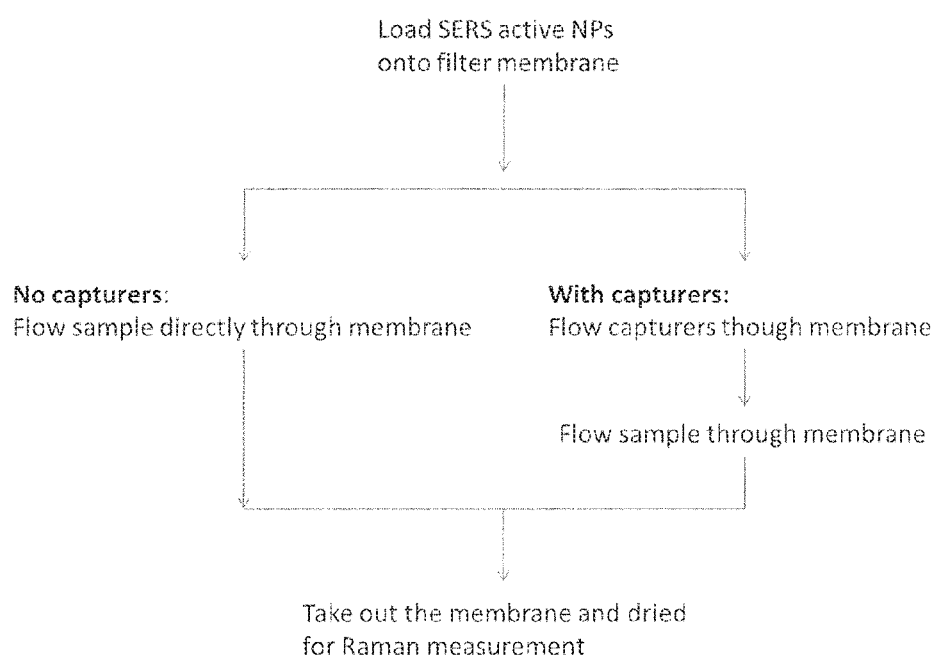
FIG. 10 is a Flow chart of one embodiment of the method of these teachings.

Experimental:

FIG. 10 shows a flow chart of the method of these teachings.

1. Prepare SERS Active NPs (e.g. Au or Ag NPs) on Filter Membranes 0.2 to 5 mL commercial or homemade SERS active NPs (e.g. Au or Ag NPs (30 to 150 nm)) were mixed with sodium or potassium salts (5 to 50 mom) to induce aggregation for 5 to 30 min. Then the NP aggregates were filtered onto a membrane slowly. In one instance, these teachings not being limited to only that instance, the membrane is a polyvinylidene fluoride (PVDF) membrane.

Figures 11A, 11B:
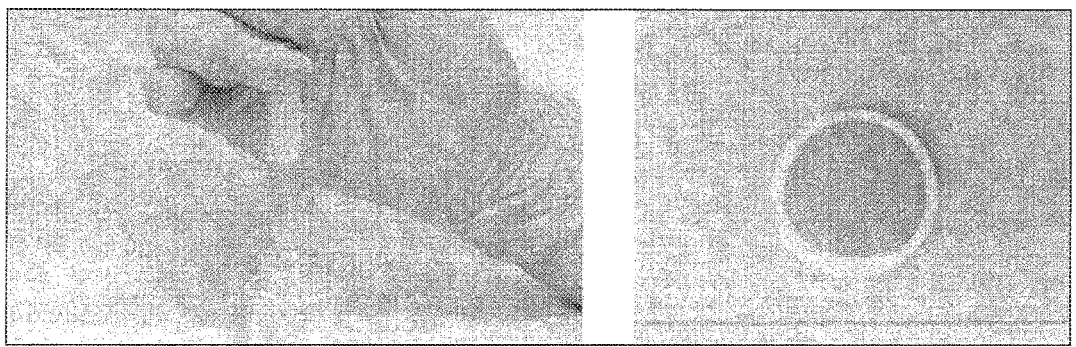
FIGS. 11a-11b show steps in preparing silver nanoparticles on filter membranes.

FIGS. 11*a*-11*b* show preparing silver nanoparticles on filter membranes.

2. Applications of the SERS Active Filter System to Detect Analytes in Water 2.1 For small chemicals: For certain targets like pesticide ferbam and antibiotic ampicillin, which can bind to Au or Ag NPs strongly and produce a sharp characteristic peaks, we can directly flow the sample (0.2 to 5 mL) through the membrane. After that, the membrane was taken out and air dried for Raman measurement.

Figure 12:
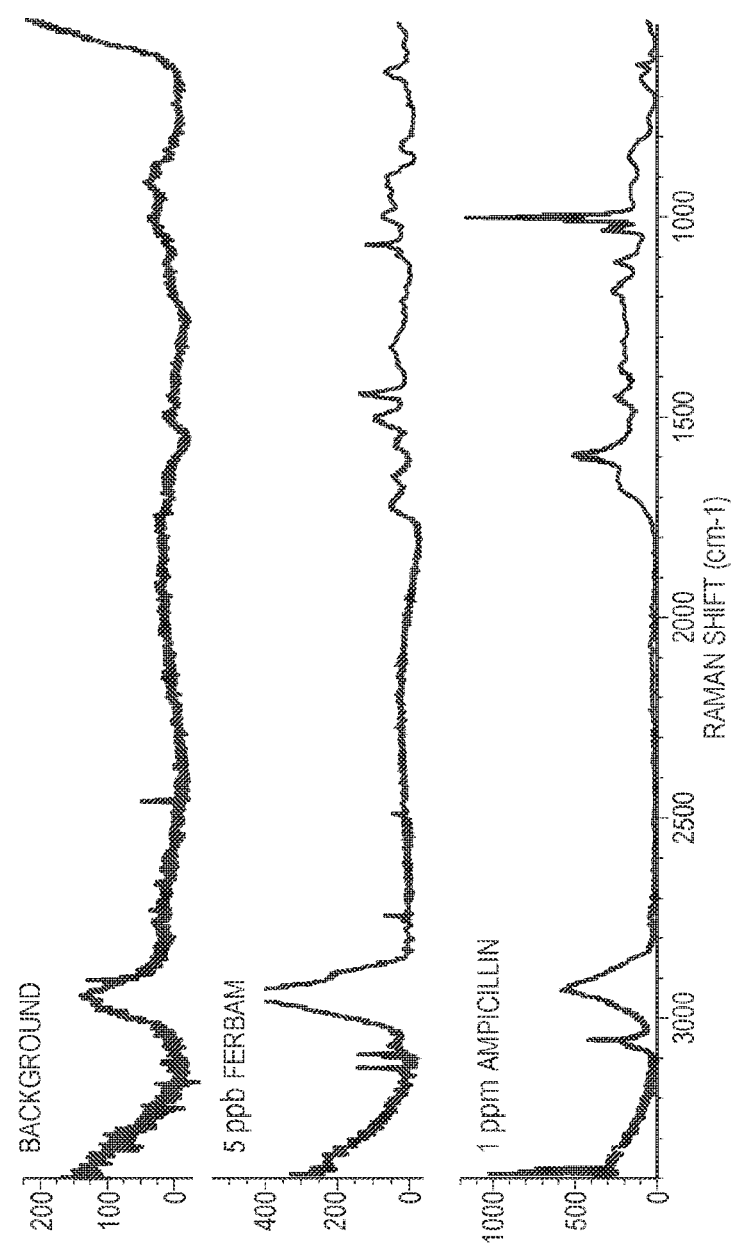
FIG. 12 shows Background signals of SERS-active membrane (red) and ferbam signals (purple) and ampicillin signals (green) on the membrane.

FIG. 12 shows results of concentrating and detecting 5 ppb ferbam in 5 mL 50% acetonitrile and 1 ppm ampicillin in 5 mL water.

As an exemplary embodiment of these teachings, the protocol used in obtaining the results of FIG. 12 is presented herein below.

Protocol

Procedure

1. Silver Nanoparticle Synthesis 1.1) Dissolve 18 mg silver nitrate in 100 mL ultrapure water (18.2 ΩU) and vortex for a few seconds.

1.2) Dissolve 20 mg sodium citrate 1 mL water and vortex for a few seconds 1.3) Transfer the silver nitrate solution to a conical flask with a stirring bar and put on a magnetic hot plate. Heat the flask under vigorous stirring.

1.4) When reach the boil, add sodium citrate solution immediately to the conical flask, and leave the solution to boil for an additional 25 min until the solution turns greenish brown, which indicates the formation of silver colloid.

1.5) Remove the flask from the hot plate and put it on another magnetic plate (do not heat) and stir overnight at the same stirring speed at room temperature until the mixture reach a stable state, with consistent a color and transparency.

1.6) Dilute the final mixture with ultrapure water to 100 mL. The colloid can be stored in the refrigerator at 4-7° C. for 2 months if needed.

2. Fabrication of a SERS active filter membrane 2.1) Dissolve 0.292 g sodium chloride (NaCl) in 100 mL water to make 5 mM NaCl solution.

2.2) Add 1 mL NaCl solution into 1 mL of prepared Ag NPs and mix on a rotator for 10 minutes. This step is to aggregate the Ag NPs into Ag nanoculsters.

2.3) Place a filter membrane (PVDF, 0.1 μm pore size) into a filter holder, which can be attached to a syringe. The smaller pore size membrane was found more effective than the larger pore size membrane (i.e. 0.22 μm) in trapping Ag nanoculsters and produce consistent signals.

2.4) Uptake 2 mL aggregated Ag nanoclusters into the syringe for filtration. Attach the filter holder to the syringe and pass the solution through the membrane at the flow rate of 1 drop/sec. The membrane traps Ag nanoclusters, forming a SERS active filter membrane.

2.5) Detach filter membrane from the filter holder, let it air dry and detect for background signal using a DXR Raman instrument (Thermo Fisher Inc.) under laser power of 1 mW and exposure time of 5 s if needed.

3. Application of the SERS Active Filter System to Detect Chemical Contaminants 3.1) Make 10 ppb ferbam solution.

3.1.1) Dissolve 2 mg ferbam in 20 mL 50% acetonitrile (10 mL acetonitrile and 10 mL water) to make stock solution (100 ppm).

3.1.2) Dilute 1 mL solution with 9 mL 50% acetonitrle.

3.1.3) Repeat the dilution procedure 3 more times to make 10 ppb ferbam solution.

3.2) Make 1 ppm ampicillin solution.

3.2.1) Dissolve 10 mg in 100 mL water to make 100 ppm ampicillin.

3.2.2) Dilute 1 mL 100 ppm solution with 9 mL water to make 10 ppm ampicillin solution.

3.2.3) Repeat the dilution procedure one more time to make 1 ppm ampicillin solution.

3.3) Put the filter membrane back to the filter holder, with the NP coated side facing up.

3.4) Load 5 mL sample into a new syringe, and then attach it to the filter holder.

3.5) Pass the sample through the membrane at the flow rate of 1 drop/sec. Target molecules can be adsorbed and concentrated onto the NPs on the filter membrane.

3.6) Detach filter membrane from the filter holder, let it air dry and measure the signals using the DXR Raman instrument under the laser power of 1 mW and exposure time of 5 s.

Important steps in the above protocol includes: 1) the Ag NPs synthesis step where uniform Ag NPs are the key for consistent results. To control the Ag NPs sizes, the heating time and the concentrations of precursors must be well controlled. 2) The salt aggregation step where the salt concentration and aggregation time must be precisely controlled. 3) The choice of membrane which smaller pore size of membrane was found more effective to trap Ag nanoculsters. In addition, for the particular membrane we used in the exemplary embodiment, the membrane has front and back sides where the front must be placed up in the holder. If it was placed down, the coating was much less effective.

2.2. For large protein molecules: For some targets like ricin proteins, which the signals were very weak and hard to differentiate between other protein signals, a specific capturer molecule (e.g. aptamer) that is specific to capture the ricin is needed (see.

To conjugate the capturer, the membrane with NPs was taken out and dried first. Then the membrane was immersed into a capturer contained buffer (see, for example, He, L., Lamont, E., Veeregowda, B., Sreevatsan, S., Haynes, C. L., Diez-Gonzalez, F., and Labuza, T. P. (2011) Aptamer-based Surface-Enhanced Raman Scattering Detection of Ricin in Liquid Foods. Chem. Sci. 2, 1579-1582, which is incorporated by reference herein in its entirety and for all purposes.) Thiolated aptamer molecules were conjugated onto Au or Ag NPs through Au—SH or Ag—SH bonds. Then the membrane were taken out of the solution and rinsed with just buffer and put back into the holder. If no immediate experiment is needed, the membrane can be dried and refrigerated for a few days. To use the aptamer functionalized SERS-active membrane, a key step is to activate the aptamer by filtering the activation buffer before applying the samples. (The activation buffer is the same as the selection buffer for aptamer. Different aptamer has different selection buffer, but a typical selection buffer contains 20 mM Tris, pH 7.5, 100 mM sodium chloride, and 5 mM magnesium chloride.)

Figure 13:
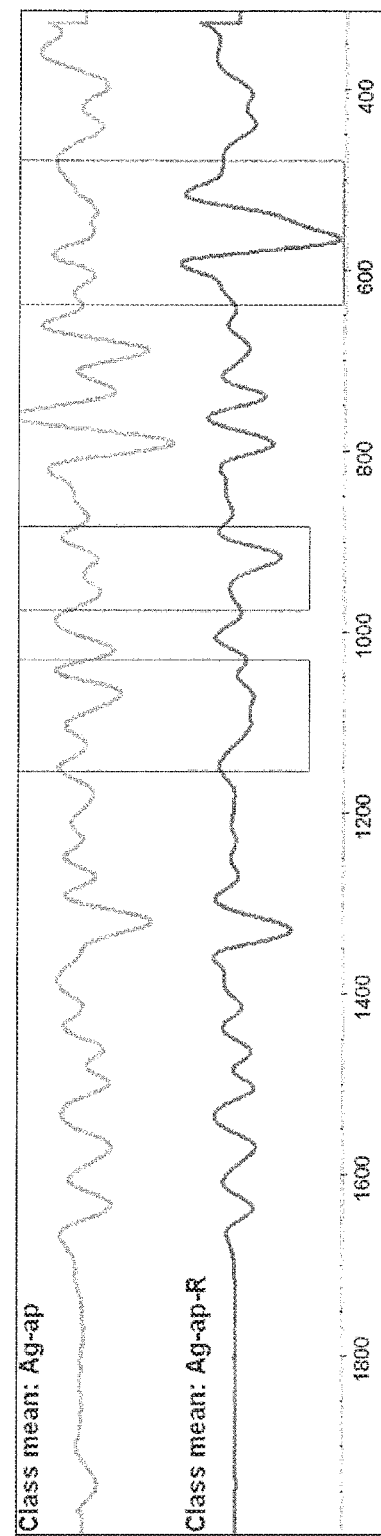
FIG. 13 shows background signals of aptamer functionalized SERS substrate (green) and the ricin protein signals captured by the aptamer on the membrane (boxed in red)

FIG. 13 shows Background signals of aptamer functionalized SERS substrate (green) and the ricin protein signals captured by the aptamer on the membrane (boxed in red).

Although the teachings have been described with respect to various embodiments, it should be realized these teachings are also capable of a wide variety of further and other embodiments within the spirit and scope of the appended claims.

What is claimed is:

1. A method, based on label-free surface-enhanced Raman scattering (SERS) mapping, for detecting bacterial cells in bacterial mixtures, the method comprising:

capturing bacterial cells on a SERS substrate comprising nanostructures that are silver nanoparticles, gold nanoparticles, silver dendrites, or mixtures thereof, the nanoparticles located on a solid support, wherein individual bacterial cells are bound by individual bacterial capturers that are conjugated to individual nanoparticles and comprise a boronic acid;

collecting from the SERS substrate with the captured bacterial cells, using a Raman microscope, a number of spectra at each pixel in a defined area of a pixelated detector;

generating a false color map of predetermined spectral regions; and detecting the captured bacterial cells from the false color map.

2. The method of claim 1 further comprising a bacterial capture is selected from selective capturers and nonselective capturers.

3. The method of claim 2 wherein the bacterial capturer is a selective capturer and the selective capturer is an aptamer.

4. The method of claim 1 wherein the SERS substrate comprises silver dendrites.

5. The method of claim 2 wherein bacterial capturers are conjugated onto the SERS substrate.

6. The method of claim 5 wherein the bacterial capturer is selected from selective capturers and nonselective capturers.

7. The method of claim 5 wherein the bacterial capturer is a nonselective capturer.

8. The method of claim 4 wherein the SERS substrate is mounted on a solid support.

9. The method of claim 8 wherein the solid support is a slide.

10. The method of claim 9 wherein capturing bacterial cells comprises:
fixedly placing the slide in a vessel;
adding a liquid sample to the vessel, the liquid sample comprising the bacterial mixture;
moving the vessel in order to makes the liquid sample and the slide; and
drying the slide after a predetermined incubation period.

11. The method of claim 10 further comprising removing excess liquid sample before drying the slide.

12. The method of claim 4 wherein capturing bacterial cells comprises:
mixing the silver dendrites with a liquid sample, the liquid sample comprising the bacterial mixture;
removing, after incubation, excess liquid sample;
placing the silver dendrites on a solid support; and
drying the solid support on which the silver dendrites are placed.

13. The method of claim 12 wherein the silver dendrites are functionalized with a bacterial capturer.

14. The method of claim 1 wherein a pore size of the membrane is less than about 0.22 μm.

15. The method of claim 1 wherein a pore size of the membrane is less than about 0.10 μm.

16. The method of claim 1, wherein the nanoparticles are filtered onto a membrane.

17. The method of claim 1, wherein the bacteria capturer comprises 4mercaptophenylboronic acid.

* * * * *

UNITED STATES PATENT AND TRADEMARK OFFICE
CERTIFICATE OF CORRECTION

PATENT NO. : 10,241,053 B2
APPLICATION NO. : 15/173098
DATED : March 26, 2019
INVENTOR(S) : Lili He Page 1 of 1

It is certified that error appears in the above-identified patent and that said Letters Patent is hereby corrected as shown below:

In the Claims

In Column 16, Line 23, in Claim 17, delete "4mercaptophenylboronic" and insert --4-mercaptophenylboronic-- therefor Signed and Sealed this
Twenty-first Day of April, 2020

Andrei Iancu
*Director of the United States Patent and Trademark Office*